(12) United States Patent
Inoue et al.

(10) Patent No.: US 7,252,748 B2
(45) Date of Patent: Aug. 7, 2007

(54) NOX MEASUREMENT APPARATUS

(75) Inventors: Yoshinori Inoue, Komaki (JP); Shinji Kumazawa, Iwakura (JP); Akihiro Kobayashi, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 768 days.

(21) Appl. No.: 10/607,191

(22) Filed: Jun. 27, 2003

(65) Prior Publication Data

US 2004/0050696 A1   Mar. 18, 2004

(30) Foreign Application Priority Data

Jun. 28, 2002   (JP) .............................. 2002-189588

(51) Int. Cl.
 *G01N 27/41* (2006.01)
(52) U.S. Cl. ...................... 204/426; 205/781; 73/23.31
(58) Field of Classification Search ................ 204/425, 204/426; 205/781, 784.5; 73/23.31
See application file for complete search history.

(56) References Cited

U.S. PATENT DOCUMENTS 5,340,462 A * 8/1994 Suzuki ........................ 204/425

5,980,710 A * 11/1999 Kurokawa et al. .......... 204/425

FOREIGN PATENT DOCUMENTS

EP          0937979 A2  *  8/1999
JP          2001-141696     5/2001

* cited by examiner

*Primary Examiner*—Kaj K. Olsen
(74) *Attorney, Agent, or Firm*—Sughrue Mion, PLLC

(57) ABSTRACT

NOx sensor element of oxygen-ion conductive solid electrolyte body 15; flow passage (7, 5, 8, 6) provided within the body for introducing analyte gas; oxygen partial pressure detection cell 3; first oxygen pump cell 1 for controlling oxygen partial pressure of the gas in the flow passage; and nitrogen oxides detection cell 2 for decomposing nitrogen oxides in the gas having a controlled oxygen partial pressure and for causing dissociated oxygen to migrate through the solid electrolyte body (see FIG. 1). Operational amplifier 22b is connected between the nitrogen oxides detection cell 2 and a 12 V battery power source to generate a voltage applied to the nitrogen oxides detection cell 2; and diode 22d connected to a point between the operational amplifier 22b and the nitrogen oxides detection cell. The diode clamps the voltage to an activation voltage higher than the measurement voltage during activation.

11 Claims, 5 Drawing Sheets

FIG. 1(B)

1) EXHAUST GAS ENTERS THE FIRST MEASUREMENT CHAMBER THROUGH THE FIRST DIFFUSION HOLE.

2) OXYGEN WITHIN EXHAUST GAS IS PUMPED OUT BY THE FIRST OXYGEN PUMP CELL. AT THAT TIME, THE OXYGEN PARTIAL PRESSURE WITHIN THE FIRST MEASUREMENT CHAMBER IS CONTROLLED BY A SIGNAL FROM THE OXYGEN PARTIAL PRESSURE DETECTION CELL.

3) AFTER HAVING BEEN CONTROLLED IN THE FIRST MEASUREMENT CHAMBER TO CONSTANT OXYGEN PARTIAL PRESSURE, EXHAUST GAS ENTERS THE SECOND MEASUREMENT CHAMBER THROUGH THE SECOND DIFFUSION HOLE.

4) NOx IN THE SECOND MEASUREMENT CHAMBER IS DECOMPOSED TO N2 AND O2, AND OXYGEN IS PUMPED OUT BY THE SECOND OXYGEN PUMP CELL.

5) AT THAT TIME, PUMP CURRENT $I_{p2}$ FLOWS IN PROPORTION TO NOx CONCENTRATION OF EXHAUST GAS.

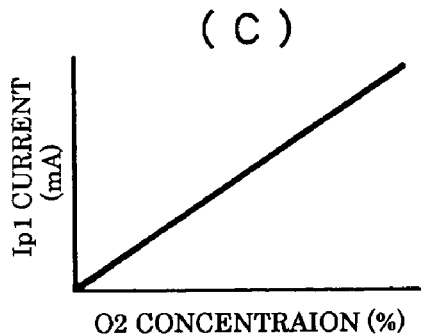

(C)

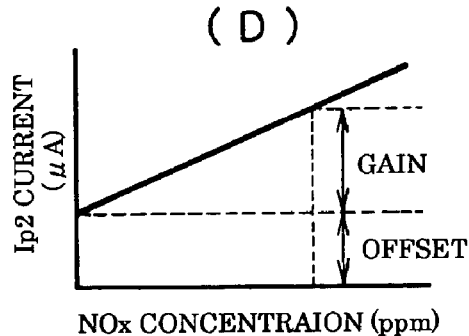

(D)

RESULTS OF COMPARISON OF Ip2 AND Vp2 WAVEFORMS

NOX MEASUREMENT APPARATUS

FIELD OF THE INVENTION

The present invention relates to an NOx measurement apparatus, and more particularly to an NOx measurement apparatus mounted on a vehicle and adapted to measure NOx (nitrogen oxides) concentration of exhaust gas of an internal combustion engine.

DESCRIPTION OF THE RELATED ART

In Patent Document 1 (Japanese Patent Application Laid-Open (kokai) No. 2001-141696), there is proposed an NOx measurement apparatus in which at the time of sensor startup, a second control voltage higher than a first control voltage for ordinary operation is applied across an NOx sensor cell for a predetermined period of time in order to remove oxygen adsorbed on the negative electrode of the NOx sensor cell, thereby shortening a stabilization time required by the sensor cell before starting proper operation.

Patent Document 1

Japanese Patent Application Laid-Open (kokai) No. 2001-141696 A

However, when high voltage is applied across an NOx sensor cell, electrodes and solid electrolyte layers that constitute the cell may be damaged. Incidentally, a battery that outputs a voltage of about 12 to 14 volts is mounted on a vehicle. Therefore, according to general practice, the battery voltage is lowered to a predetermined voltage and the predetermined voltage is applied across an NOx sensor cell. However, the above-described Japanese Patent Application Laid-Open No. 2001-141696 does not disclose any method for producing such a voltage to be applied across the NOx sensor cell.

SUMMARY OF THE INVENTION

An object of the present invention is to provide an NOx measurement apparatus which can shorten the time before the apparatus starts stable operation, while securing safety of a sensor element, by use of a simple and inexpensive configuration. Further objects will become apparent from the entire disclosure including claims and drawings.

The principle of the present invention will be described. When a high voltage is applied across a nitrogen oxides detection cell of the NOx sensor element which utilizes solid electrolyte, the solid electrolyte that constitutes the cell permits flow of oxygen contained in the solid electrolyte itself, whereby the solid electrolyte may be blackened or metalized (deoxidized). The phenomenon of solid electrolyte being blackened is called "blackening."

A battery of about 12 to 14 V is mounted on an ordinary vehicle. Conventionally, battery voltage supplied from the battery is lowered in order to generate a predetermined voltage to be applied across a nitrogen oxides detection cell. Therefore, a conventional NOx measurement apparatus has a special circuit for generating a predetermined voltage to be applied across the nitrogen oxides detection cell.

Incidentally, when measurement is performed by use of the above-mentioned NOx measurement apparatus, the above-described NOx sensor element is first heated such that the above-mentioned solid electrolyte exhibits a sufficient degree of oxygen ion conductivity. This process is called "activation."

Before start of measurement, a gas having the same composition as that of the atmosphere is highly likely to remain in a flow passage provided in the NOx sensor element. That is, a gas having an oxygen concentration of 20.9% may remain in the flow passage. In order to accurately measure concentration of nitrogen oxides, the oxygen partial pressure within the flow passage must be lowered to a sufficient degree. Further, in order to quickly start measurement, during a period for the above-described activation, it is necessary not only to heat the NOx sensor cell, but also to apply the possible highest voltage across the nitrogen oxides detection cell, to thereby pump oxygen out of the flow passage or a nitrogen oxides-concentration measurement chamber.

Immediately after the start of activation, the temperature of the solid electrolyte remains low, and thus, the nitrogen oxides detection cell has a high internal resistance. Therefore, even if the magnitude of current flowing through the nitrogen oxides detection cell is small, the voltage applied across the nitrogen oxides detection cell becomes excessively high, because of the high internal resistance of the nitrogen oxides detection cell, which raises the possibility of occurrence of blackening.

In view of the foregoing, in order to prevent application of high voltage across the nitrogen oxides detection cell, there may be employed a scheme in which instead of voltage (normally 12 V) of a battery mounted on a vehicle, a power source of, for example, 5 V is used, in combination with an ordinary operational amplifier, in order to generate a voltage to be applied across the nitrogen oxides detection cell. However, an ordinary amplifier whose power source voltage is 5 V has a narrow output voltage range of 1.5 to 3.5 V, and cannot apply a sufficiently high voltage across the nitrogen oxides detection cell, in particular, at the time of activation. Therefore, there occurs a problem that a long time is needed to start measurement. If such an NOx measurement apparatus were used for measurement of nitrogen oxides concentration of exhaust gas of a vehicle, there would occur a problem that so-called "light-off" is slow. (In general, the reference potential of a sensor is set to 2 to 3 V, in order to cause positive or negative flow of first oxygen pump current ($Ip1$) in accordance with whether exhaust gas is lean or rich. In such a case, the potential difference that can be applied to the sensor decreases further.)

Moreover, when a "Rail-to-Rail" scheme operational amplifier having a wide output voltage range is used as means for generating voltage to be applied across a nitrogen oxides detection cell, there arises a problem that such a "Rail-to-Rail" scheme operational amplifier is very expensive.

An NOx measurement apparatus according to the present invention includes clamp means which is disposed between the nitrogen oxides detection cell and means for generating voltage to be applied across the nitrogen oxides detection cell, and which clamps the voltage applied across the nitrogen oxides detection cell to a voltage which is to be applied across the nitrogen oxides detection cell before start of measurement and which is higher than a predetermined voltage to be applied across the nitrogen oxides detection cell during measurement. This configuration enables application of an optimum voltage across the nitrogen oxides detection cell during activation of an NOx sensor element or immediately after the activation, wherein the optimum voltage is higher than a predetermined voltage applied across the nitrogen oxides detection cell during ordinary measurement but does not cause damage to the cell. The clamp means provided in the NOx measurement apparatus enables an operation of safely applying the possible highest voltage to the nitrogen oxides detection cell to thereby remove oxygen from the flow passage as quickly as possible. Therefore, wait time before start of measurement can be shortened. Accordingly, when the NOx measurement apparatus of the present invention is applied to measurement of nitrogen oxides concentration of exhaust gas of a vehicle, the light-off can be made quicker. In addition, when the NOx measurement apparatus of the present invention is applied to measurement of nitrogen oxides concentration of exhaust gas of a vehicle, an existing battery on the vehicle; e.g., a 12 V battery, can be used as a power source for generating the voltage to be applied across the nitrogen oxides detection cell. Therefore, the necessity of providing a separate low-voltage power source, such as a 5-V power source, and providing a special circuit for driving a 5 V-type operation amplifier can be eliminated. Moreover, the present invention renders an expensive "Rail-to-Rail" scheme operational amplifier unnecessary.

According to a first aspect of the present invention, there is provided an NOx measurement apparatus which comprises an NOx sensor element. The NOx sensor element includes: a flow passage to which an analyte gas is introduced; an oxygen partial pressure detection cell for detecting oxygen concentration of the analyte gas introduced to the flow passage; a first oxygen pump cell for pumping oxygen out of the interior of the flow passage to the exterior of the flow passage, or for pumping oxygen into the interior of the flow passage from the exterior of the flow passage, on the basis of the oxygen concentration detected by the oxygen partial pressure detection cell, so that current corresponding to the oxygen concentration of the gas introduced to the flow passage flows through the first oxygen pump cell; and a second oxygen pump cell to which the analyte gas having an oxygen concentration controlled by the first oxygen pump cell flows and which decomposes nitrogen oxides within the gas and causes oxygen dissociated from the nitrogen oxides to migrate, wherein a predetermined voltage is applied across the second oxygen pump cell, and the nitrogen oxides concentration of the analyte gas is measured based on current flowing through the second oxygen pump cell.

The NOx measurement apparatus is characterized by:
(1) voltage generation means, connected between the second oxygen pump cell and a power source, for generating, from a voltage supplied from the power source, a voltage to be applied across the second oxygen pump cell; and
(2) clamp means, connected between the voltage generation means and the second oxygen pump cell, for clamping the voltage applied across the second oxygen pump cell to a predetermined voltage which is higher than a predetermined measurement voltage to be applied across the second oxygen pump cell during measurement but not higher than a voltage supplied from the power source.

According to a second aspect of the present invention, there is provided an NOx measurement apparatus which comprises an NOx sensor element which in turn includes: a first measurement chamber to which an analyte gas is introduced via a first diffusion resistance; an oxygen partial pressure detection cell having two electrodes provided at the interior and exterior, respectively, of the first measurement chamber and adapted to detect oxygen concentration of the analyte gas within the first measurement chamber on the basis of a potential difference between the electrodes of the oxygen partial pressure detection cell; a first oxygen pump cell having two electrodes provided at the interior and exterior, respectively, of the first measurement chamber and adapted to pump oxygen out of the interior of the first measurement chamber to the exterior of the first measurement chamber, or pump oxygen into the interior of the first measurement chamber from the exterior of the first measurement chamber, through the electrodes of the first oxygen pump cell, whereby a current (hereinafter referred to as "first oxygen pump current") corresponding to oxygen concentration of the analyte gas flows between the electrodes of the first oxygen pump cell; a second measurement chamber to which the analyte gas is introduced from the first measurement chamber via a second diffusion resistance; and a second oxygen pump cell having two electrodes provided at the interior and exterior, respectively, of the second measurement chamber and adapted to decompose nitrogen oxides within the second measurement chamber and cause oxygen dissociated from the nitrogen oxides to migrate, whereby a current (hereinafter referred to as "second oxygen pump current") corresponding to NOx concentration of the analyte gas flows across the electrodes of the second oxygen pump cell. The NOx measurement apparatus further comprises: oxygen-partial-pressure-detection-cell control means for controlling oxygen concentration on the exterior-side electrode of the oxygen partial pressure detection cell; first-oxygen-pump-cell control means for controlling the first oxygen pump current by applying a predetermined voltage across the first oxygen pump cell on the basis of a detection signal output from the oxygen partial pressure detection cell to thereby control the oxygen concentration within the first measurement chamber; second-oxygen-pump-cell control means for applying a predetermined measurement voltage across the second oxygen pump cell in order to control the second oxygen pump cell in such a manner that second oxygen pump current corresponding to the NOx concentration flows through the second oxygen pump cell; activation means for applying a high voltage across the second oxygen pump cell when the second oxygen pump cell is to be activated, the high voltage being higher than the predetermined voltage to be applied across the second oxygen pump cell during ordinary measurement; second-oxygen-pump-current detection means for detecting the second oxygen pump current; and clamp means, connected between the second oxygen pump cell and the second-oxygen-pump-cell control means and the activation means, and adapted to limit the voltage applied across the second oxygen pump cell to a voltage (or less) which is to be applied across the second oxygen pump cell during activation of the second oxygen pump cell.

According to the present invention, during a period in which the second oxygen pump cell is activated, the voltage applied across the second oxygen pump cell is clamped and limited by the clamp means. Therefore, damage to the second oxygen pump cell is prevented, and thus the safety of the sensor element is secured. In addition, since the clamp means is connected between the second oxygen pump cell and the second-oxygen-pump-cell control means for driving the second oxygen pump cell, a voltage higher than the activation voltage to be applied across the second oxygen pump cell during activation can be used as a power source voltage of the second-oxygen-pump-cell control means. In an example case in which the activation voltage is 5 V, an operational amplifier whose power source voltage is 12 V (voltage of a battery mounted on a vehicle) can be used instead of an expensive "Rail-to-Rail" operational amplifier which requires a 5-V power source. Therefore, a special circuit for generating an activation voltage of 5 V becomes unnecessary, and circuits such as the second-oxygen-pump-cell control means can be configured simply.

According to a third aspect of the invention, there in provided an NOx measurement apparatus which comprises an NOx sensor element. The NOx measurement apparatus includes: an oxygen-ion-conductive solid electrolyte, a flow passage which is disposed within or adjacent to said solid electrolyte and to which an analyte gas is introduced; an oxygen partial pressure detection cell for detecting oxygen partial pressure of the analyte gas introduced to the flow passage; a first oxygen pump cell for controlling the oxygen partial pressure of said analyte gas introduced to the flow passage by pumping oxygen out of the interior of the flow passage to the exterior of the flow passage, or by pumping oxygen into the interior of the flow passage from the exterior of the flow passage based on the oxygen partial pressure detected by the oxygen partial pressure detection cell; and a nitrogen oxides detection cell which causes dissociated oxygen resulting from decomposition of nitrogen oxides in the gas controlled for the oxygen partial pressure to migrate within said solid electrolyte, wherein a predetermined voltage is applied across said nitrogen oxides detection cell, and the nitrogen oxides concentration of the analyte gas is measured based on a current flowing through said solid electrolyte.

The NOx measurement apparatus is characterized by:
(1) voltage generation means, connected between said nitrogen oxides detection cell and a power source, for generating, from a voltage supplied from the power source, a voltage to be applied across said nitrogen oxides detection cell; and
(2) clamp means, connected between the voltage generation means, for generating a voltage to be applied across said nitrogen oxides detection cell, and said nitrogen oxides detection cell, for always preventing an over-voltage applied across said nitrogen oxides detection cell and allowing a voltage which is sufficiently higher than a measurement voltage to be applied across said nitrogen oxides detection cell during activation of said NOx sensor element.

BRIEF DESCRIPTION OF THE DRAWINGS

[FIG. 1]
FIGS. 1(A) to 1(D) are diagrams and graphs for schematically explaining the structure of an NOx sensor element, which is a component of an NOx measurement apparatus according to an embodiment of the present invention, as well as a measurement principle.

FIG. 3(A) is a diagram for schematically explaining second-oxygen-pump-cell control means provided in an NOx measurement apparatus according to Reference Example 1, and 3(B) is a diagram for schematically explaining clamp means and second-oxygen-pump-cell control means provided in the NOx measurement apparatus according to the embodiment of the present invention.

FIG. 4 is a graph for explaining results of measurement of Vp2 and Ip2 performed for the NOx measurement apparatus of the embodiment of the present invention (Example 1), the NOx measurement apparatus of Reference Example 1, and the NOx measurement apparatus of Reference Example 2.

DETAILED DESCRIPTION OF THE PREFERRED EMBODIMENTS

Figure 1A:
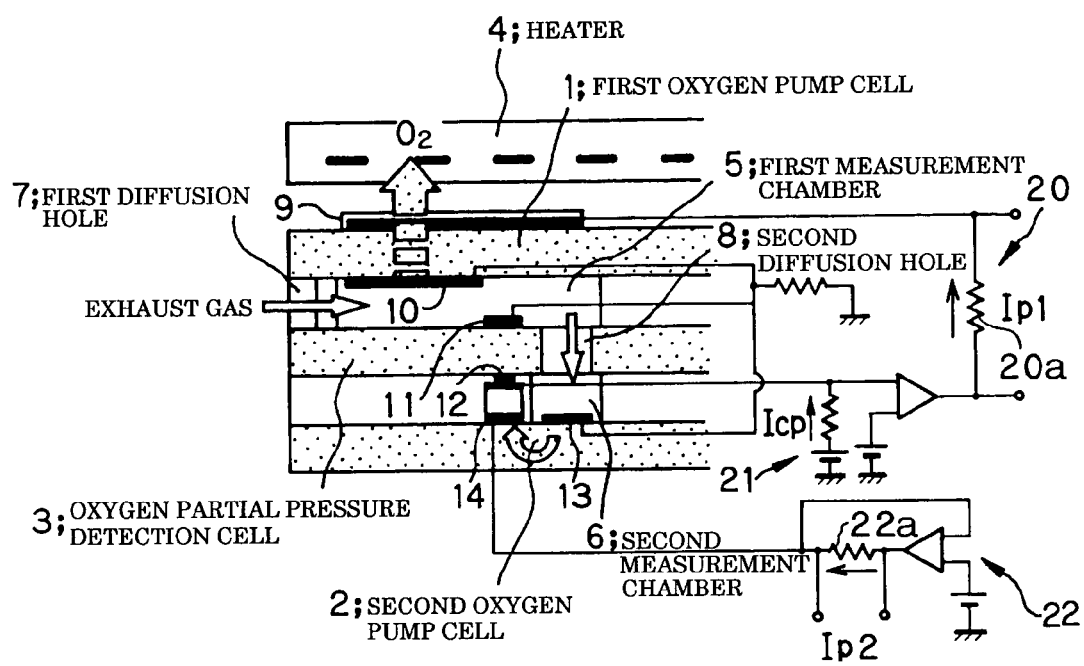

An NOx measurement apparatus according to a preferred mode of the present invention includes an oxygen-ion conductive solid electrolyte body 15; a flow passage (7, 5, 8, 6) which is provided within a solid electrolyte body or adjacent to the solid electrolyte body and to which an analyte gas is introduced; an oxygen partial pressure (concentration) detection cell 3 for detecting oxygen partial pressure of the analyte gas introduced to the flow passage; an oxygen pump cell (a first oxygen pump cell 1) for pumping oxygen out of the interior of the flow passage to the exterior of the flow passage, or for pumping oxygen into the interior of the flow passage from the exterior of the flow passage, on the basis of the oxygen partial pressure detected by the oxygen partial pressure detection cell to thereby control the oxygen partial pressure of the gas introduced to the flow passage; and a nitrogen oxides detection cell (a second oxygen pump cell 2) for decomposing nitrogen oxides within the analyte gas having a controlled oxygen partial pressure and for moving dissociated oxygen through the solid electrolyte body. The NOx measurement apparatus further comprises voltage generation means 22b which is connected between the nitrogen oxides detection cell and a power source (e.g., a 12 V battery power source mounted on a vehicle) and is adapted to generate, from a voltage supplied from the power source, a voltage to be applied across the nitrogen oxides detection cell; and clamp means 22d connected between the voltage generation means and the nitrogen oxides detection cell and adapted to clamp the voltage applied across the nitrogen oxides detection cell to a voltage (hereinafter referred to as "activation voltage") which is to be applied across the nitrogen oxides detection cell during activation of the NOx sensor element and which is higher than a predetermined voltage (hereinafter referred to as "measurement voltage") to be applied across the nitrogen oxides detection cell during measurement. In other words, the clamp means always prevent the application of an overvoltage across the nitrogen oxides detection cell when an extraordinary large voltage is about to be applied across the nitrogen oxides detection cell, whereas the clamp means allow the application of a sufficient large voltage during activation of the NOx sensor element as compared to that during the measurement.

Figure 3:
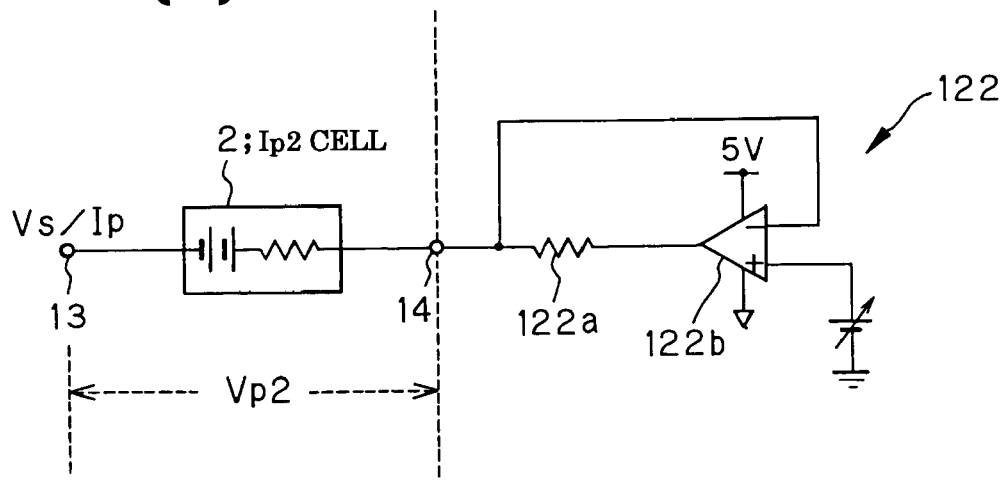
[FIG. 3]
Figure 3:
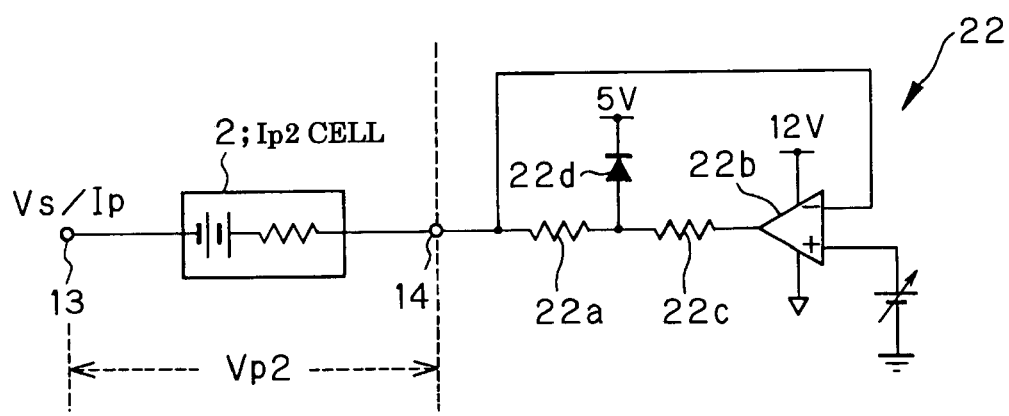

More preferably, the voltage generation means includes an amplification circuit 22b having a power source terminal for receiving drive voltage from the power source (see a power source terminal of FIG. 3(B) to which, e.g., 12 V is input), a non-inverted input terminal (+) for receiving a variably set input voltage, and an inverted input terminal (−) and an output terminal which are connected to each other (see an inverted input terminal (−) and an output terminal of FIG. 3(B), which are electrically connected to each other via a feed back resistance); and the clamp means includes a diode 22d which is connected to a node between the inverted input terminal and the output terminal and which enters a conductive state when a voltage higher than the activation voltage is applied to the nitrogen oxides detection cell, to thereby clamp and limit the voltage applied to the nitrogen oxides detection cell to the activation voltage or less.

Preferably, a circuit for generating the activation voltage by changing the amplification ratio of the amplification circuit (see an activation means 40 of FIG. 2) is connected between the inverted input terminal and the output terminal.

Preferably, the circuit for generating the activation voltage is configured in such a manner that the voltage output from the amplification circuit assumes a level ranging from the measurement voltage to plus about 2 V or 3 V, in consideration of voltage drop caused by current flowing through a detection resistance 22a and a resistance 22c. Further, immediately after the activation voltage is applied across the nitrogen oxides detection cell (the second oxygen pump cell), the above-described input voltage is changed in such a manner that a voltage that is 1 to 15% higher than the measurement voltage is applied across the nitrogen oxides detection cell.

The NOx measurement apparatus of the present invention is advantageously applied to an apparatus for measuring nitrogen oxides concentration of exhaust gas discharged from an internal combustion engine mounted on a vehicle; and a battery power source for driving or controlling the internal combustion engine is used as the power source for driving the voltage generation means 22b for generating the voltage to be applied across the nitrogen oxides detection cell.

In the preferred mode of the present invention, the second-oxygen-pump-current detection means includes a detection resistance through which the second oxygen pump-current flows; the second-oxygen-pump-cell control means includes an operational amplifier for controlling the voltage applied across the second oxygen pump cell to a predetermined value; and the clamp means includes a diode (22d in FIG. 3(B)) connected to a node between the detection resistance (22a in FIG. 3(B)) and the output terminal of the operational amplifier (22b in FIG. 3(B)).

EXPERIMENTAL EXAMPLES

In order to further clarify the above-described preferred mode of the present invention, an embodiment of the present invention will now be described with reference to the drawings.

FIGS. 1(A) to 1(D) are diagrams and graphs used to explain the structure of an NOx sensor element, which is a component of an NOx measurement apparatus according to the embodiment of the present invention, as well as a measurement principle.

Referring to FIG. 1(A), the NOx sensor element mainly includes a first oxygen pump cell (oxygen pump cell) 1, a second oxygen pump cell (nitrogen oxides detection cell) 2, an oxygen partial pressure detection cell 3, and a heater 4 for heating the NOx sensor element to a predetermined operation temperature. A first measurement chamber 5 is formed between the first oxygen pump cell 1 and the oxygen partial pressure detection cell 3. An analyte gas is introduced to the first measurement chamber 5 through a first diffusion hole 7. The first measurement chamber 5 communicates with a second measurement chamber 6 via a second diffusion hole 8. In other words, a flow passage (7, 8, 5, 6) is provided within a solid electrolyte body (or adjacent to the solid electrolyte body).

The first oxygen pump cell 1 is constituted by a solid electrolyte having oxygen-ion conductivity, such as zirconia, and paired electrodes 9 and 10 formed on the solid electrolyte. The electrode 10 is disposed to face the first measurement chamber 5, whereas the electrode 9 is disposed to face the outside. Oxygen ions which are generated on the electrode 10 as a result of dissociation of oxygen, etc. within the first measurement chamber 5 are caused to pass through the solid electrolyte and escape to the outside from the electrode 9. Current that flows through the solid electrolyte at that time serves as a first oxygen pump current Ip1.

The second oxygen pump cell 2 is constituted by a solid electrolyte having oxygen-ion conductivity, such as zirconia, and paired electrodes 13 and 14 formed on the solid electrolyte. The electrode 13 is disposed to face the second measurement chamber 6, whereas the electrode 14 is disposed outside the second measurement chamber 6, and is exposed to an atmosphere whose oxygen concentration is stable. Oxygen ions which are generated on the electrode 13 as a result of dissociation of NOx, etc. within the second measurement chamber 6 are caused to pass through the solid electrolyte and escape to the outside from the electrode 14. Current that flows through the solid electrolyte at that time serves as a second oxygen pump current Ip2. In an ordinary measurement mode, a constant voltage is applied across the electrodes 13 and 14.

The oxygen partial pressure detection cell 3 is constituted by a solid electrolyte having oxygen-ion conductivity, such as zirconia, and paired electrodes 11 and 12 formed on the solid electrolyte. The electrode 11 is disposed to face the first measurement chamber 5, whereas the electrode 12 is exposed to an atmosphere whose oxygen concentration is stable. Therefore, the oxygen concentration within the first chamber 5; i.e., the oxygen concentration of the analyte gas, can be detected on the basis of potential difference generated between the electrodes 11 and 12.

Referring to FIG. 1(A), sensor control means is composed of oxygen-partial-pressure-detection-cell control means 21 which detects oxygen concentration within the first measurement chamber 5 on the basis of a signal appearing from the oxygen partial pressure detection cell 3 and controls oxygen concentration on the electrode 12 disposed outside the first measurement chamber 5; first-oxygen-pump-cell control means 20 which controls the first oxygen pump current Ip1 on the basis of a detection output from the oxygen partial pressure detection cell 3 to thereby maintain the oxygen concentration within the first measurement chamber 5 constant to an extent possible; and second-oxygen-pump-cell control means 22 which applies voltage to the second oxygen pump cell 2, while maintaining the voltage constant to an extent possible, to thereby control the second oxygen pump cell 2 in such a manner that second oxygen pump current Ip2 corresponding to NOx concentration flows through the second oxygen pump cell 2. The first oxygen pump current Ip1 and the voltage Vp1 applied across the first oxygen pump cell 1 can be detected through measurement of current flowing through a detection resistance 20a of the first-oxygen-pump-cell control means 20 and through measurement of voltage across the detection resistance 20a, respectively. The second oxygen pump current Ip2 and the voltage Vp2 applied across the second oxygen pump cell 2 can be detected through measurement of current flowing through a detection resistance 22a of the second-oxygen-pump-cell control means 22 and through measurement of voltage across the detection resistance 22a, respectively.

Figure 2:
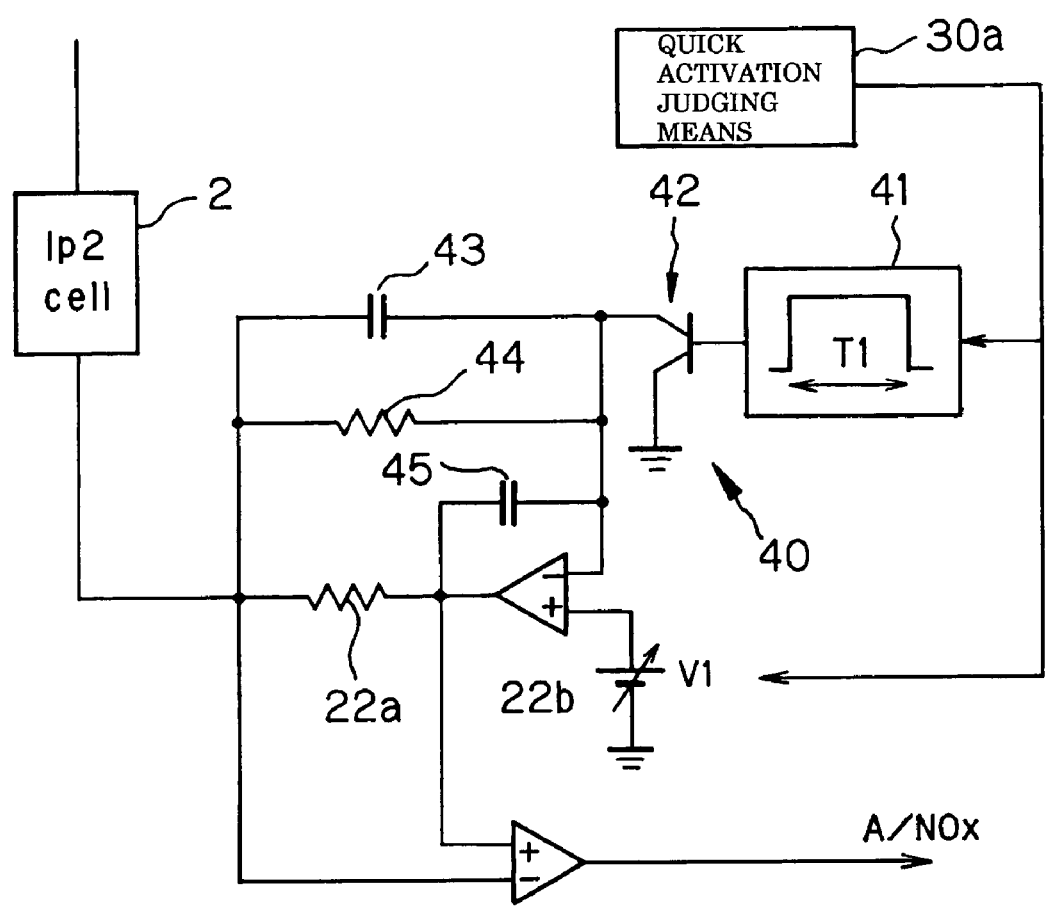
[FIG. 2]
Diagram for schematically explaining means for activating a second oxygen pump cell which is applied to the NOx measurement apparatus shown in FIG. 1(A).

FIG. 2 is a diagram showing means for activating the second oxygen pump cell which is applied to the NOx measurement apparatus shown in FIG. 1(A). Referring to FIG. 2, activation means 40 for activating the second oxygen pump cell 2 includes quick activation judging means 30a; a timer 41 which outputs a one-short pulse signal in response to an instruction output from the quick activation judging means 30a; a transistor 42 which is connected to the output of the timer 41 and is driven in response to the one-shot pulse signal, serving as an ON signal; and an integration circuit comprised of a capacitor 43 and a resistance 44 and connected to the collector terminal of the transistor 42. A node between the transistor 42 and the integration circuit is connected to a non-inverted input terminal of an operational amplifier 22*b*. A node between the capacitor 43 and the resistance 44 is connected to a node between the detection resistance 22*a* and the second oxygen pump cell 2. A capacitor 45 is connected between the inverted input terminal and an output terminal of the operational amplifier 22*b*, making up a sort of voltage follower. Further, a power source is connected to a non-inverted input terminal of the operational amplifier 22*b* of the second-oxygen-pump-cell control means 22. In response to an instruction from the quick activation judging means 30*a*, the power source outputs different values (i.e. change the value) of the voltage V1 (input voltage of the operational amplifier 22*b*) in an activating period and in a non-activating period, such as measurement period.

When the timer 41 turns the transistor 42 on in response to an instruction from the quick activation judging means 30*a*, the amplification ratio of the operational amplifier 22*b* changes, whereby a voltage higher than that applied during an ordinary measurement period is applied across the second oxygen pump cell 2.

FIG. 3(A) is a diagram showing a second-oxygen-pump-cell control means provided in an NOx measurement apparatus according to Reference Example 1, whereas FIG. 3(B) is a diagram showing clamp means and second-oxygen-pump-cell control means provided in an NOx measurement apparatus according to the embodiment of the present invention.

As shown in FIG. 3(A), the second-oxygen-pump-cell control means 122 provided in the NOx measurement apparatus according to Reference Example 1 has an operational amplifier 122*b*, which, making up a sort of voltage follower, receives power from a 5-V power source. By contrast, the second-oxygen-pump-cell control means 22 provided in the NOx measurement apparatus according to the embodiment of the present invention has an operational amplifier 22*b*, which, making up a sort of voltage follower, receives power from a 12-V power source. A resistance 22*c* is connected between the detection resistance 22*a* and the output terminal of the operational amplifier 22*b*, and a diode (clamp means) 22*d* is connected to a node between the resistance 22*c* and the detection resistance 22*a* in order to clamp and limit the voltage applied across the second oxygen pump cell 2 to 5 V or less. The diode 22*d* serving as a clamp (or clipping) means is connected between the second oxygen pump cell 2 and the second-oxygen-pump-cell control means 22 and the activation means 40 (see FIG. 2) and limits the voltage applied across the second oxygen pump cell 2 to a voltage to be supplied to the second oxygen pump cell 2 during an activating period. That is, when the transistor 42 (see FIG. 2) is turned on in response to an activation instruction output from the quick activation judging means 30*a* (see FIG. 2) with the result that the voltage of the output terminal of the operational amplifier 22*b* increases to reach a predetermined level or greater, the diode 22*d* enters a conductive state, whereby the voltage (potential) at one electrode 14 of the second oxygen pump cell 2 is clamped and limited to 5 V or less. As aforementioned, the potential of the electrode 13 (Vs/Ip terminal), i.e., the reference voltage is usually set at 2 to 4 V. On the other hand, the voltage applied across the second oxygen pump cell (Ip2 cell) (i.e., potential difference between the electrodes 13 and 14) is set by the resistances 22*a* and 22*c* so as to assume an optimum value approximately of 400 to 550 mV. This potential difference is a voltage that can sufficiently activate the Ip2 cell and that does not cause the electrodes of the Ip2 cell blacking (deoxidization). According to the present invention, the potential at the node between the resistance 22*a* and the resistance 22*c* is biased by the diode 22*d* so as not to exceed 5 V. Thus, the voltage applied across the Ip2 cell can be set to such optimum value by setting the total resistance of the resistances 22*a* and 22*c* to e.g., an order of 200 to 400 K ohm. Thus, the safety of the sensor element is secured.

In the NOx measurement apparatus of Reference Example 1, since a Rail-to-Rail operational amplifier is employed, cost of the measurement apparatus increases, and when the measurement apparatus is applied to measurement of NOx concentration of exhaust gas of an internal combustion engine of a vehicle, a special power source circuit for lowering the voltage of an onboard battery in order to generate 5 V becomes necessary. By contrast, in the NOx measurement apparatus according to the embodiment of the present invention, since a 12 V-drive operational amplifier 22*b* can be used, the NOx measurement apparatus can be manufactured at low cost, and the above-mentioned special power source circuit for generating 5 V becomes unnecessary.

Figure 4:
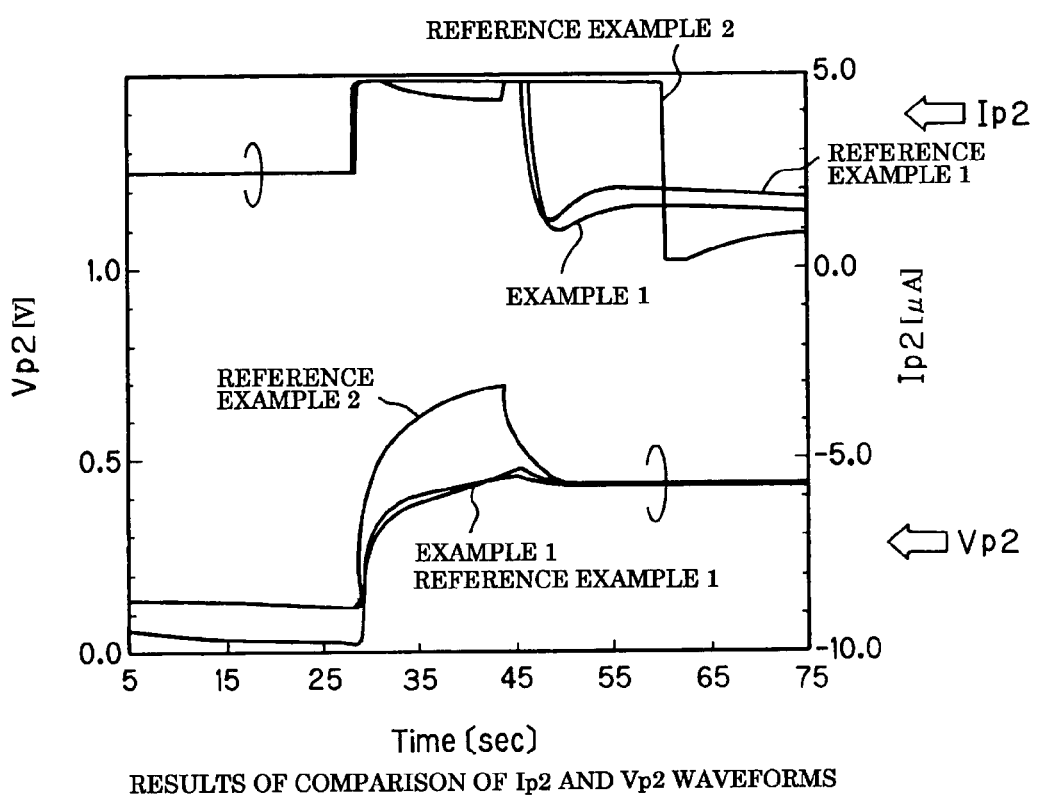
[FIG. 4]

FIG. 4 is a graph showing results of measurement of Vp2 and Ip2 performed for the NOx measurement apparatus of the embodiment of the present invention (Example 1), the NOx measurement apparatus of Reference Example 1, and an NOx measurement apparatus of Reference Example 2. The NOx measurement apparatus of Reference Example 2 is identical with that of Example 1 shown in FIG. 3(B), except that the diode 22*d* is not provided. The measurement conditions are as follows. It is set that the voltage Vp2 applied across the second oxygen pump cell 2 (voltage between both the electrodes) under the stable state assumes about 0.45 V, and in Example 1 and Reference Example 2 a 12 V-driven operational amplifier was used, whereas in the Reference Example 1 a 5 V-driven operational amplifier was used.

As can be seen from FIG. 4, in the NOx measurement apparatus of Example 1, the voltage Vp2 applied across the second oxygen pump cell and the second oxygen pump current Ip2 flowing through the second oxygen pump cell are greatly reduced as compared with those of the NOx measurement apparatus of Reference Example 2. According to Reference Example 2, there is fear for generation of blacking in the second oxygen pump cell because the voltage actually applied across the second oxygen pump cell exceeds an allowable expected value if the voltage to be applied across the second oxygen pump cell is set to a high voltage at the rising time of the sensor in order to remove oxygen in the flow passage rapidly. Therefore, it offers a problem, according to Reference Example 2, that a voltage to be applied across the second oxygen pump cell cannot be raised to a sufficient high value at the rising time of the sensor (during the activation of the sensor). On the other hand, Example 1 shows that the provision of the clamp means (diode 22*d*) assures always to limit the voltage applied across the second oxygen pump cell to a predetermined value, and thus the wait time required before starting with a measurement at the time of start of the sensor operation (activation time of the sensor) through setting the voltage applied across the second oxygen pump cell at a high value can be reduced. Accordingly, it is understood that in the NOx measurement apparatus of Example 1, the second oxygen pump current Ip2 flowing through the second oxygen pump cell is reduced further as compared with that of the NOx measurement apparatus of Reference Example 1.

The meritorious effect of the present invention are summarized as follows.

According to the present invention, there is provided an NOx measurement apparatus which can shorten the time before the apparatus starts stable operation, while securing safety of a sensor element, by use of a simple and inexpensive configuration.

It should be noted that other objects, features and aspects of the present invention will become apparent in the entire disclosure and that modifications may be done without departing the gist and scope of the present invention as disclosed herein and claimed as appended herewith.

Also it should be noted that any combination of the disclosed and/or claimed elements, matters and/or items may fall under the modifications aforementioned.

This application is based on Japanese Patent Application No. 2002-189588 filed Jun. 28, 2003, incorporated herein by reference in its entirety.

What is claimed is:

1. An NOx measurement apparatus comprising an NOx sensor element which includes:
   a flow passage to which an analyte gas is introduced;
   an oxygen partial pressure detection cell for detecting oxygen concentration of the analyte gas introduced to the flow passage;
   a first oxygen pump cell for pumping oxygen out of the interior of the flow passage to the exterior of the flow passage, or for pumping oxygen into the interior of the flow passage from the exterior of the flow passage, on the basis of the oxygen concentration detected by the oxygen partial pressure detection cell, so that current corresponding to the oxygen concentration of the gas introduced to the flow passage flows through the first oxygen pump cell; and
   a second oxygen pump cell to which the analyte gas having an oxygen concentration controlled by the first oxygen pump cell flows and which decomposes nitrogen oxides within the gas and causes oxygen dissociated from the nitrogen oxides to migrate, wherein
   a predetermined voltage is applied across the second oxygen pump cell, and the nitrogen oxides concentration of the analyte gas is measured based on current flowing through the second oxygen pump cell,
   the NOx measurement apparatus further comprising:
   voltage generation means, connected between the second oxygen pump cell and a power source, for generating, from a voltage supplied from the power source, a voltage to be applied across the second oxygen pump cell; and
   clamp means, connected between the voltage generation means and the second oxygen pump cell, for clamping the voltage applied across the second oxygen pump cell to a predetermined voltage which is higher than a predetermined measurement voltage to be applied across the second oxygen pump cell during measurement and which is at a level that does not damage the second oxygen pump cell but less than the voltage supplied from the power source, wherein said voltage supplied from the power source is at a level which would damage the second oxygen pump cell if applied directly thereto.

2. An NOx measurement apparatus according to claim 1, wherein
   the voltage generation means includes an amplification circuit having a power source terminal for receiving drive voltage from the power source, a non-inverted input terminal for receiving a variably set input voltage, and an inverted input terminal and an output terminal which are connected to each other; and
   the clamp means includes a diode which is connected to a node between the inverted input terminal and the output terminal and which enters a conductive state when a voltage higher than the predetermined voltage is applied across the second oxygen pump cell, to thereby limit the voltage applied across the second oxygen pump cell to the predetermined voltage or below.

3. An NOx measurement apparatus according to claim 2, wherein a circuit is connected between the inverted input terminal and the output terminal of the amplification circuit, and is adapted to change the amplification ratio of the amplification circuit, when the NOx sensor element or the second oxygen pump cell is activated, in order to generate a voltage higher than the voltage applied across the second oxygen pump cell during ordinary measurement.

4. An NOx measurement apparatus according to claim 3, wherein immediately after the predetermined voltage is applied across the second oxygen pump cell when the NOx sensor element or the second oxygen pump cell is activated, the input voltage is changed in such a manner that a voltage close to and greater than the measurement voltage is applied across the second oxygen pump cell.

5. An NOx measurement apparatus according to claim 1, wherein
   the NOx measurement apparatus measures nitrogen oxides concentration of exhaust gas discharged from an internal combustion engine mounted on a vehicle; and
   the power source is a battery power source for driving or controlling the internal combustion engine.

6. An NOx measurement apparatus according to claim 1, wherein
   the flow passage is formed by a first diffusion resistance, a first measurement chamber to which the analyte gas is introduced via the first diffusion resistance; a second diffusion resistance, and a second measurement chamber to which the gas is introduced via the second diffusion resistance from the first measurement chamber;
   the NOx sensor element includes said oxygen partial pressure detection cell having two electrodes provided at the interior and exterior, respectively, of the first measurement chamber and adapted to detect oxygen concentration of the analyte gas within the first measurement chamber based on a potential difference between the electrodes of the oxygen partial pressure detection cell; a first oxygen pump cell having two electrodes provided at the interior and exterior, respectively, of the first measurement chamber and adapted to pump oxygen out of the interior of the first measurement chamber to the exterior of the first measurement chamber, or pump oxygen into the interior of the first measurement chamber from the exterior of the first measurement chamber, through the electrodes of the first oxygen pump cell, whereby a first oxygen pump current corresponding to oxygen concentration of the analyte gas flows between the electrodes of the first oxygen pump cell; a second measurement chamber to which the analyte gas is introduced from the first measurement chamber via the second diffusion resistance; and a second oxygen pump cell having two electrodes provided at the interior and exterior, respectively, of the second measurement chamber and adapted to decompose nitrogen oxides within the second measurement chamber and cause oxygen dissociated from the nitrogen oxides to migrate, whereby a second oxygen pump current corresponding to NOx concentration of the analyte gas flows between the electrodes of the second oxygen pump cell; and the NOx measurement apparatus further comprises;
oxygen-partial-pressure-detection-cell control means for controlling oxygen concentration on the external-side electrode of the oxygen partial pressure detection cell;
first-oxygen-pump-cell control means for controlling the first oxygen pump current by applying a predetermined voltage to the first oxygen pump cell based on a detection signal output from the oxygen partial pressure detection cell to thereby control the oxygen concentration within the first measurement chamber;
second-oxygen-pump-cell control means for applying a predetermined voltage to the second oxygen pump cell in order to control the second oxygen pump cell in such a manner that second oxygen pump current corresponding to the NOx concentration flows through the second oxygen pump cell;
activation means for applying a high voltage to the second oxygen pump cell when the second oxygen pump cell is to be activated, the high voltage being higher than the measurement voltage to be applied across the second oxygen pump cell during ordinary measurement;
second-oxygen-pump-current detection means for detecting the second oxygen pump current; and
clamp means, connected between the second oxygen pump cell, and the second-oxygen-pump-cell control means and the activation means, for clamping and limiting the voltage applied across the second oxygen pump cell to the predetermined voltage or less which is to be applied across the second oxygen pump cell during activation.

7. An NOx measurement apparatus according to claim 6, wherein
the second-oxygen-pump-current detection means includes a detection resistance through which the second oxygen pump-current flows;
the second-oxygen-pump-cell control means includes an operational amplifier for controlling the voltage applied across the second oxygen pump cell to a predetermined value; and
the clamp means includes a diode connected to a node between the detection resistance and the output terminal of the operational amplifier.

8. An NOx measurement apparatus as claimed in claim 1, wherein said predetermined voltage applied across the second oxygen pump cell is about 400 to about 550 mV.

9. An NOx measurement apparatus as claimed in claim 1, wherein said clamp means comprises a diode and two resistances, a terminal of the diode being connected to the two resistances.

10. An NOx measurement apparatus which comprises an NOx sensor element which includes:
an oxygen-ion-conductive solid electrolyte,
a flow passage which is disposed within or adjacent to said solid electrolyte and to which an analyte gas is introduced;
an oxygen partial pressure detection cell for detecting oxygen partial pressure of the analyte gas introduced to the flow passage;
a first oxygen pump cell for controlling the oxygen partial pressure of said analyte gas introduced to the flow passage by pumping oxygen out of the interior of the flow passage to the exterior of the flow passage, or by pumping oxygen into the interior of the flow passage from the exterior of the flow passage based on the oxygen partial pressure detected by the oxygen partial pressure detection cell; and
a nitrogen oxides detection cell which causes dissociated oxygen resulting from decomposition of nitrogen oxides in the gas controlled for the oxygen partial pressure to migrate within said solid electrolyte,
wherein
a predetermined voltage is applied across said nitrogen oxides detection cell, and the nitrogen oxides concentration of the analyte gas is measured based on a current flowing through said solid electrolyte,
said NOx measurement apparatus being characterized by comprising:
voltage generation means, connected between said nitrogen oxides detection cell and a power source, for generating, from a voltage supplied from the power source, a voltage to be applied across said nitrogen oxides detection cell, wherein said voltage supplied from the power source is at a level which would damage the nitrogen oxides detection cell if applied directly thereto; and
clamp means, connected between the voltage generation means, for generating a voltage to be applied across said nitrogen oxides detection cell, and said nitrogen oxides detection cell, for always preventing an overvoltage applied across said nitrogen oxides detection cell and allowing a voltage which is sufficiently higher than a measurement voltage but less than the voltage supplied from the power source to be applied across said nitrogen oxides detection cell during activation of said NOx sensor element.

11. An NOx measurement apparatus comprising an NOx sensor element which includes:
a flow passage to which an analyte gas is introduced;
an oxygen partial pressure detection cell for detecting oxygen concentration of the analyte gas introduced to the flow passage;
a first oxygen pump cell for pumping oxygen out of the interior of the flow passage to the exterior of the flow passage, or for pumping oxygen into the interior of the flow passage from the exterior of the flow passage, on the basis of the oxygen concentration detected by the oxygen partial pressure detection cell, so that current corresponding to the oxygen concentration of the gas introduced to the flow passage flows through the first oxygen pump cell; and
a second oxygen pump cell to which the analyte gas having an oxygen concentration controlled by the first oxygen pump cell flows and which decomposes nitrogen oxides within the gas and causes oxygen dissociated from the nitrogen oxides to migrate, wherein
a predetermined voltage is applied across the second oxygen pump cell, and the nitrogen oxides concentration of the analyte gas is measured based on current flowing through the second oxygen pump cell,
the NOx measurement apparatus further comprising:
voltage generation means, connected between the second oxygen pump cell and a power source, for generating, from a voltage supplied from the power source, a voltage to be applied across the second oxygen pump cell; and
clamp means, connected between the voltage generation means and the second oxygen pump cell, for clamping the voltage applied across the second oxygen pump cell to a predetermined voltage which is higher than a predetermined measurement voltage to be applied across the second oxygen pump cell during measurement but not higher than a voltage supplied from the power source, wherein the voltage generation means includes an amplification circuit having a power source terminal for receiving drive voltage from the power source, a non-inverted input terminal for receiving a variably set input voltage, and an inverted input terminal and an output terminal which are connected to each other; and the clamp means includes a diode which is connected to a node between the inverted input terminal and the output terminal and which enters a conductive state when a voltage higher than the predetermined voltage is applied across the second oxygen pump cell, to thereby limit the voltage applied across the second oxygen pump cell to the predetermined voltage or below.

* * * * *